(12) United States Patent
Seiler

(10) Patent No.: US 7,683,075 B2
(45) Date of Patent: Mar. 23, 2010

(54) ISOQUINOLINE-3-CARBOXYLIC ACID AMIDES AND PHARMACEUTICAL USES THEREOF

(75) Inventor: Max Peter Seiler, Riehen (CH)

(73) Assignee: Novartis AG, Basel (CH)

( * ) Notice: Subject to any disclaimer, the term of this patent is extended or adjusted under 35 U.S.C. 154(b) by 530 days.

(21) Appl. No.: 10/556,356

(22) PCT Filed: May 11, 2004

(86) PCT No.: PCT/EP2004/005042

§ 371 (c)(1),
(2), (4) Date: Aug. 11, 2006

(87) PCT Pub. No.: WO2004/099206

PCT Pub. Date: Nov. 18, 2004

(65) Prior Publication Data

US 2007/0142428 A1    Jun. 21, 2007

(30) Foreign Application Priority Data

May 12, 2003    (GB) ................................. 0310867.7

(51) Int. Cl.
*A01N 43/90* (2006.01)
*C07D 453/02* (2006.01)
(52) U.S. Cl. .................... 514/305; 546/133; 546/137
(58) Field of Classification Search ................. 546/112, 546/133, 148, 137; 514/299, 305, 307
See application file for complete search history.

(56) References Cited

U.S. PATENT DOCUMENTS

| 7,001,900 | B2 * | 2/2006 | Jacobsen et al. | ....... 514/214.03 |
| 2005/0107425 | A1 * | 5/2005 | Rogers et al. | ................ 514/304 |
| 2005/0245504 | A1 * | 11/2005 | Corbett et al. | ......... 514/214.01 |
| 2006/0019984 | A1 * | 1/2006 | Groppi et al. | ................ 514/305 |

FOREIGN PATENT DOCUMENTS

| EP | 0 311 724 A1 | 4/1989 |
| EP | 0 353 371 A1 | 2/1990 |
| EP | 0 353 372 B1 | 2/1990 |
| FR | 2 625 678 A1 | 7/1989 |
| WO | WO 91/17161 A1 | 11/1991 |
| WO | WO 97/30998 A1 | 8/1997 |
| WO | WO 02/085901 A | 10/2002 |
| WO | WO 03/022856 A | 3/2003 |
| WO | WO 03/037896 A | 5/2003 |
| WO | WO 03/072578 A | 9/2003 |
| WO | WO 2004/052348 A | 6/2004 |
| WO | WO 2004/052461 A | 6/2004 |

OTHER PUBLICATIONS

Court et al., Pharmacology, Biochemistry and Behavior, vol. 70, 2001, pp. 571-579.*

* cited by examiner

*Primary Examiner*—D. Margaret Seaman
*Assistant Examiner*—Niloofar Rahmani
(74) *Attorney, Agent, or Firm*—Paul D. Strain; Fanelli, Strain & Haag, PLLC

(57) ABSTRACT

The present invention relates to novel isoquinoline-3-carboxylic acid amides having α7 nicotinic acetylcholine receptor agonistic activity, their preparation, their use as pharmaceuticals and pharmaceutical compositions containing them.

12 Claims, No Drawings

ISOQUINOLINE-3-CARBOXYLIC ACID AMIDES AND PHARMACEUTICAL USES THEREOF

The present invention relates to novel isoquinoline-3-carboxylic acid amides having α7 nicotinic acetylcholine receptor agonistic activity, their preparation, their use as pharmaceuticals and pharmaceutical compositions containing them.

More particularly the invention provides a compound of formula I

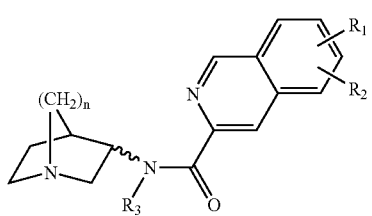

wherein $R_1$ and $R_2$, independently, are hydrogen, $(C_{1-4})$alkyl, halogen, hydroxy, $(C_{1-4})$alkoxy, di$(C_{1-4})$alkylamino, $(C_{1-4})$alkylthio, cyano or trifluoromethyl, $R_3$ is hydrogen or $(C_{1-4})$alkyl and n is 1 or 2, in free base or acid addition salt form.

Halogen denotes fluorine, bromine, chlorine or iodine.

Any alkyl, alkoxy or alkylthio groups are branched or straight chain groups. They are preferably methyl, methoxy or methylthio groups. n is preferably 2.

On account of the asymmetrical carbon atom(s) present in the compounds of formula I and their salts, the compounds may exist in optically active form or in form of mixtures of optical isomers, e.g. in form of racemic mixtures. All optical isomers and their mixtures including the racemic mixtures are part of the present invention.

(S)-1-azabicyclo[2.2.2]oct-2-yl-amino and (S)-1-azabicyclo[2.2.1]hept-2-yl-amino compounds are preferred.

In a further aspect, the invention provides a process for the production of the compounds of formula I and their salts, comprising the step or reacting a compound of formula II

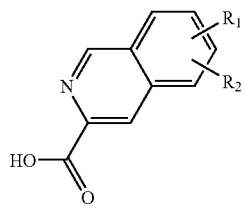

wherein $R_1$ and $R_2$ are as defined above, with a compound of formula III

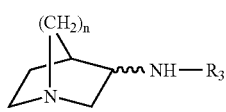

wherein $R_3$ and n are as defined above, and recovering the resulting compound of formula I in free base or acid addition salt form.

The reaction can be effected according to conventional methods, e.g. as described in the examples.

Working up the reaction mixtures according to the above processes and purification of the compounds thus obtained may be carried out in accordance to known procedures.

Acid addition salts may be produced from the free bases in known manner, and vice versa.

Compounds of formula I in optically pure form can be obtained from the corresponding racemates according to well-known procedures. Alternatively, optically pure starting materials can be used.

The starting compounds of formula II may be obtained by conventional methods e.g. by oxidation of compounds of formula IV or V

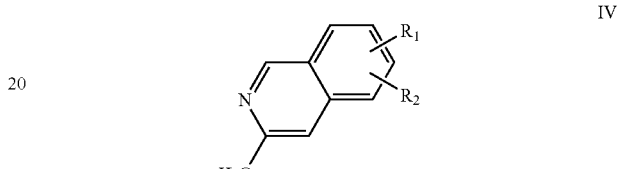

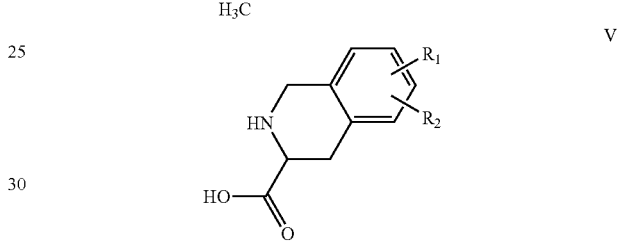

wherein $R_1$ and $R_2$ are as defined above, according to conventional methods.

The starting materials of formula III, IV and V are known or may be obtained from known compounds, e.g. as described in the Examples.

Compounds of formula I and their pharmaceutically acceptable acid addition salts, hereinafter referred to as agents of the invention, exhibit valuable pharmacological properties when tested in vitro and in animals, and are therefore useful as pharmaceuticals.

In particular, the agents of the invention are α7 nicotinic acetylcholine receptor (nAChR) agonists.

In functional assays, the agents of the invention display high affinity at the α7 nAChR as shown in the following tests:

a) A functional assay for affinity at α7 nAChR is carried out with a rat pituitary cell line stably expressing the α7 nAChR. As a read out, the calcium influx upon stimulation of the receptor is used. In this assay, agents of the invention exhibit $pEC_{50}$ values of about 5 to about 8.

b) To assess the selectivity of the agents of the invention, a similar functional assay is carried out using a human epithelial cell line stably expressing the neuronal α4β2 nAChR subtype. In this assay, agents of the invention display no or little activity at the α4β2 nAChR.

c) To assess the selectivity of the compounds of the invention, similar functional assays as described under a) are carried out with a human epithelial cell line stably expressing the ganglionic nAChR subtype or a cell line endogenously expressing the muscle type of nicotinic receptors. In these assays, agents of the invention display no or little activity on the ganglionic and muscle type of nicotinic receptor subtypes.

In the model of mice showing sensory gating deficit (DBA/2-mice) described by S. Leonard et al. in Schizophrenia Bulletin 22, 431-445 (1996), the agents of the invention induce significant sensory gating at concentrations of about 10 to about 40 µM.

The agents of the invention are therefore useful for the treatment of psychotic disorders such as schizophrenia, mania, depression and anxiety, and for the treatment of neurodegenerative disorders such as senile dementia, Alzheimer's disease and other intellectual impairment disorders, such as attention deficit hyperactivity disorders (ADHD), cognitive dysfunctions and memory deficits; Parkinson's disease, Huntington's chorea, amyotrophic lateral sclerosis and multiple sclerosis, furthermore for the treatment of pain, epilepsy and inflammatory disorders such as rheumatoid arthritis and Crohn's disease. The usefulness in inflammatory disorders is based on the finding that α-7 agonists reduce TNF release from macrophages, as reported in Wang et al., Nature, 2002:421, 384. The usefulness of α7 nAChR agonists in neurodegeneration is also documented in the literature, e.g. in Wang et al., J. biol. Chem. 275, 5626-5632 (2000).

For the above-mentioned indications, the appropriate dosage will of course vary depending upon, for example, the compound employed, the host, the mode of administration and the nature and severity of the condition being treated. However, in general, satisfactory results in animals are indicated to be obtained at a daily dosage of from about 0.01 to about 100, preferably from about 0.1 to about 50 mg/kg animal body weight. In larger mammals, for example humans, an indicated daily dosage is in the range from about 1 to about 500, preferably from about 5 to about 300 mg of an agent of the invention conveniently administered, for example, in divided doses up to four times a day or in sustained release form.

The agent of the invention may be administered by any conventional route, in particular enterally, preferably orally, for example in the form of tablets or capsules, or parenterally, for example in the form of injectable solutions or suspensions.

In accordance with the foregoing, the present invention also provides an agent of the invention, for use as a pharmaceutical, e.g. for the treatment of any condition mentioned above.

The present invention furthermore provides a pharmaceutical composition comprising an agent of the invention in association with at least one pharmaceutical carrier or diluent. Such compositions may be manufactured in conventional manner. Unit dosage forms contain, for example, from about 0.25 to about 150, preferably from about 1 to about 25 mg of a compound according to the invention.

Moreover the present invention provides the use of an agent of the invention, for the manufacture of a medicament for the treatment of any condition mentioned above.

In still a further aspect the present invention provides a method for the treatment of any condition mentioned above, in a subject in need of such treatment, which comprises administering to such subject a therapeutically effective amount of an agent of the invention.

The following examples illustrate the invention.

EXAMPLE 1

Isoquinoline-3-carboxylic acid{(S)-1-azabicyclo[2.2.2]oct-2-yl}-amide 529 mg of isoquinoline-3-carboxylic acid hydrate are dissolved in 18 ml of DMF, followed by addition of 508 mg of 1-hydroxy-benzotriazol and 1.81 g of dicyclohexyl-carbodiimide. After stirring for 1 h at r.t., the precipitated dicylohexyl-urea is filtered off and 500 mg of 3(S)-aminoquinuclidine dihydrochloride and 1.3 ml of ethyl-diisopropylamine is added to the filtrate. After stirring for 48 h at room temperature, a second portion of dicylohexyl-urea is filtered off and washed with MeOtBu/DMF (4:1). Wash solution and filtrate are combined and crystallized by standing over night at 5°. The crystalline precipitate is filtered off and washed with MeOtBu/DMF (4:1), followed by MeOtBu to yield the title compound as monohydrochloride.

NMR ($^1$H, 400 MHz, $\delta_H$ d$_6$-DMSO): 1.75 (1H, t), 1.96 (2H, m); 2.12 (1H, q), 2.24 (1H, d), 3.24 (3H, m), 3.43 (2H, m), 3.65 (1H, t), 4.49 (1H, q), 7.86 (1H, t), 7.92 (1H, t), 8.24 (1H, d), 8.30 (1H, d), 8.61 (1H, s), 9.31 (1H, d), 9.46 (1H, s), 10.59 (1H, br).

MS (ES$^+$): 282 (MH)$^+$

EXAMPLE 2

Isoquinoline-3-carboxylic acid{(R)-1-azabicyclo[2.2.2]oct-2-yl}-amide

The compound is prepared as monohydrochloride according to Example 1 starting from 3(R)-aminoquinuclidine and isoquinoline-3-carboxylic acid hydrate.

NMR ($^1$H, 400 MHz, $\delta_H$ d$_6$-DMSO): 1.76 (1H, t), 1.96 (2H, q), 2.12 (1H, q), 2.24 (1H, d), 3.22 (3H, m), 3.45 (2H, m), 3.64 (1H, t), 4.49 (1H, q), 7.88 (1H, t), 7.96 (1H, t), 8.25 (1H, d), 8.33 (1H, d), 8.71 (1H, s), 9.38 (1H, d), 9.49 (1H, s), 10.77 (1H, s).

MS (ES$^+$): 282 (MH)$^+$

EXAMPLE 3

6-Fluoro-isoquinoline-3-carboxylic acid{(R)-1-azabicyclo[2.2.2]oct-2-yl}-amide

The compound is prepared according to Example 1 starting from 3(R)-aminoquinuclidine and 6-fluoroquinoline-3-carboxylic acid. Further purification is achieved by chromatography on silica gel eluting with MeOtBu/EtOH/conc. aqu. NH$_3$ (75/22.5/2.5).

NMR ($^1$H, 400 MHz, $\delta_H$ d$_6$-DMSO): 1.38 (1H, m), 1.63 (2H, dt), 1.78 (1H, m), 1.93 (1H, q), 2.65-2.80 (4H, m), 2.94 (1H, dt), 3.18 (1H, dt), 4.06 (1H, m), 7.72 (1H, dt), 8.04 (1H, dd), 8.39 (1H, q), 8.57 (1H, s), 8.76 (1H, d), 9.42 (1H, s).

MS (ES$^+$): 300 (MH)$^+$

The starting material can be prepared as follows:

6-Fluoro-isoquinoline-3-carboxylic acid hydrochloride 2.15 g of 6-fluoro-1,2,3,4-tetrahydro-isoquinoline-3-carboxylic acid methyl ester are dissolved in 120 ml of xylene. 1.6 g of Pd—C (10%) is added and the suspension is refluxed during 8 h. The catalyst is filtered off, washed with MeOH and the filtrate, combined with the wash solution, evaporated to dryness.

1 g of the resulting crude 6-fluoro-isoquinoline-3-carboxylic acid methyl ester is dissolved in 20 ml of MeOH/THF (1:1) and slowly mixed at 5° with a solution of 510 mg of LiOH hydrate in 10 ml of water. The resulting solution is stirred at room temperature overnight and poured into a solution consisting of 50 ml of MeOtBu, 10 ml of water and 7 ml of 2N aqu. HCl. The precipitate is filtered off and washed with MeOtBu.

NMR ($^1$H, 400 MHz, $\delta_H$ d$_6$-DMSO): 7.77 (1H, dt), 8.04 (1H, dd), 8.38 (1H, dt), 8.66 (1H, s), 9.43 (1H, s).

MS (ES$^-$): 190 (M-H)$^-$

6-Fluoro-1,2,3,4-tetrahydro-isoquinoline-3-carboxylic acid methyl ester 2 g of m-fluoro-DL-phenylalanine are suspended in 20 ml of conc. hydrochloric acid and 8 ml of aqu. 37% formaldehyde solution and stirred during 3.5 h at 90° during which a partial solution takes place. Stirring is continued overnight at room temperature and the precipitate filtered off and washed with cold water. Filtrate, combined with the wash solutions are evaporated to dryness, the residue suspended in 50 ml of MeOH saturated with HCl and stirred overnight, during which a clear solution is formed. The solvent is evaporated, the residue dissolved in CH$_2$Cl$_2$/MeOH (9:1) and extracted with 2N Na$_2$CO$_3$ solution and brine. The organic phases are dried over Na$_2$SO$_4$, evaporated and chromatographed on silica gel using MeOtBu. The title compound is obtained as an oil, MS (ES$^+$): 210 (MH)$^+$.

In addition, 6-fluoro-3-methyl-1,2,3,4-tetrahydro-isoquinoline-3-carboxylic acid methyl ester and 8-fluoro-1,2,3,4-tetrahydro-isoquinoline-3-carboxylic acid methyl ester can be isolated as byproducts.

EXAMPLE 4

8-Fluoro-isoquinoline-3-carboxylic acid{(R)-1-azabicyclo[2.2.2]oct-2-yl}-amide

The title compound is prepared according to Example 1 starting from 3(R)-aminoquinuclidine and 8-fluoro-isoquinoline-3-carboxylic acid. Further purification is achieved by chromatography on silica gel eluting with MeOtBu/EtOH/conc. aqu. NH$_3$ (80/18/2).

NMR ($^1$H, 400 MHz, $\delta_H$ d$_6$-DMSO): 1.38 (1H, m), 1.63 (2H, dt), 1.78 (1H, m), 1.93 (1H, q), 2.64-2.81 (4H, m), 2.93 (1H, dt), 3.17 (1H, dt), 4.07 (1H, m), 7.63 (1H, dt), 7.90 (1H, dd), 8.09 (1H, d), 8.63 (1H, s), 8.79 (1H, d), 9.53 (1H, s).

MS (ES$^+$): 300 (MH)$^+$

The starting material can be prepared as follows:

8-Fluoro-isoquinoline-3-carboxylic acid hydrochloride

The compound is prepared by oxidation of 8-fluoro-1,2,3,4-tetrahydro-isoquinoline-3-carboxylic acid methyl ester, followed by saponification according to the preparation of 6-fluoro-isoquinoline-3-carboxylic acid (Example 3).

NMR ($^1$H, 400 MHz, $\delta_H$ d$_6$-DMSO): 7.68 (1H, dd), 7.92 (1H, dd), 8.09 (1H, d), 8.71 (1H, s), 9.57 (1H, s).

MS (ES$^-$): 190 (M-H)$^-$

8-Fluoro-1,2,3,4-tetrahydro-isoquinoline-3-carboxylic acid methyl ester

The compound is obtained as a byproduct during the synthesis of 6-fluoro-1,2,3,4-tetrahydro-isoquinoline-3-carboxylic acid methyl ester (see Example 3).

MS (EI): 209 (M$^+$)

EXAMPLE 5

8-Fluoro-isoquinoline-3-carboxylic acid{(S)-1-azabicyclo[2.2.2]oct-2-yl}-amide

2-Fluoro-6-iodo-benzaldehyde

Buthyllithium (1.6 M, 60 ml, 0.113 mol) is added to an ice cooled solution of diisopropyl-amine (17.6 ml, 0.124 mol) in THF (200 ml). The solution is stirred at 0° C. for 30 minutes and is cooled to −78° C. 1-Fluoro-3-iodo-benzene (25 g, 0.113 mol) in THF (20 ml) is slowly added to the preformed LDA mixture. The resulting solution is stirred for another hour after which DMF (9.55 ml, 0.124 mol) is added and stirring is continued for another 30 minutes at −78° C. The reaction is quenched first with acetic acid (20 ml) followed by water (200 ml). The mixture is extracted with ether. The organic layer is washed with a 2N HCl solution, brine, is dried over MgSO$_4$ and evaporated to afford the desired compound (28.3 g).

2-(2-Fluoro-6-iodo-phenyl)-[1,3]dioxane

2-Fluoro-6-iodo-benzaldehyde (3.0 g, 12 mmol), 1,3-propanediol (1.3 ml, 18 mmol), and para-toluenesulfonic acid (342 mg, 1.8 mmol) is heated at reflux in toluene (60 ml) using a Dean-Stark apparatus for 2 hours. The organic layer is washed with brine and dried over MgSO$_4$ and evaporated to afford the desired compound (3.65 g).

2-Acetylamino-3-(2-[1,3]dioxan-2-yl-3-fluoro-phenyl)-acrylic acid methyl ester

A DMF (10 ml) solution of 2-(2-fluoro-6-iodo-phenyl)-[1,3]dioxane (1.85 g, 6 mmol), 2-acetylamino-acrylic acid methyl ester (906 mg, 6.33 mmol), sodium bicarbonate (1.26 g, 15 mmol), tetrabutyl ammonium chloride (1.35 g, 4.86 mmol) and palladium (II) acetate (52 mg, 0.23 mmol) is heated at 90° C. for 1.8 hours. The reaction mixture is poured onto water and the aqueous phase is extracted with ethylacetate. The organic layer is washed with brine and dried over MgSO$_4$ and evaporated. The crude product is purified by chromatography (CH$_2$Cl$_2$/MeOH, 95/5) to afford the desired compound (240 mg). MS (ES$^+$): m/e=346.3, (MNa$^+$)

8-Fluoro-isoquinoline-3-carboxylic acid methyl ester

2-Acetylamino-3-(2-[1,3]dioxan-2-yl-3-fluoro-phenyl)-acrylic acid methyl ester (10.6 g, 32.8 mmol) and pyridinium para-toluene sulfonate (2.06 g, 8.2 mmol) are heated to reflux for 20 hours in an acetone/water (120 ml/15 ml) mixture. The solvents are removed by evaporation and the aqueous residue is extracted with ethylacetate. The organic layer is washed with brine and dried over MgSO$_4$ and evaporated. The crude product is recrystallised from ethylacetate/ether to afford 5.1 g of the desired compound. MS (ES$^+$): m/e=206.2 (MH$^+$)

8-Fluoro-isoquinoline-3-carboxylic

Lithium hydroxide (525 mg, 21.93 mmol) is added to a solution of 8-Fluoro-isoquinoline-3-carboxylic acid methyl ester (1.5 g, 7.31 mmol) in methanol (63 ml) and water (7 ml).

The solution is stirred at room temperature for 18 hours. The solvent mixture is removed by evaporation and the residue is redissolved in a methanol/water mixture. The resulting solution is acidified to pH1 using a concentrated HCl solution. The methanol is removed and the crystals are gathered by filtration and dried to afford 1.05 g of the desired compound.

8-Fluoro-isoquinoline-3-carboxylic acid{(S)-1-azabicyclo[2.2.2]oct-2-yl}-amide

Dicyclohexyl-carbodiimide (7.69 g, 30 mmol) is added to a solution of 8-fluoro-isoquinoline-3-carboxylic acid (5.1 g, 22.4 mmol), ethyl-diisopropyl-amine (4.6 ml, 26.88 mmol) and hydroxybenzotriazole (5.36 g, 33.6 mmol) in DMF (150 ml). The mixture is stirred for 2 hours at room temperature. (S)-(1-Aza-bicyclo[2.2.2]oct-3-yl)amine (4.46 g, 49.28 mmol) and ethyl-diisopropyl-amine (8.7 ml, 49.28 mmol) are added and the solution is stirred for another 18 hours at room temperature. The solvent is removed by evaporation and the residue is dissolved in methylenedichloride and washed with a saturated $K_2CO_3$ solution and brine. The organic layer is dried over $MgSO_4$ and evaporated. The crude product is purified by chromatography ($CH_2Cl_2$/MeOH/$NH_4OH$, 92.5/7.5/0.75) to afford the desired compound (2.35 g). The product is recrystallized from ethanolic HCl to give 2 g. of the hydrochloric salt.

MS (ES$^+$): m/e=300 (MH$^+$)

The invention claimed is:

1. A compound of formula I

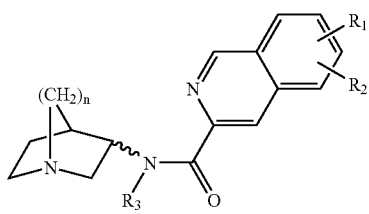

wherein $R_1$ and $R_2$, independently, are hydrogen, ($C_{1-4}$) alkyl, halogen, hydroxy, ($C_{1-4}$)alkoxy, di($C_{1-4}$)alkylamino, ($C_{1-4}$)alkylthio, cyano or trifluoromethyl, $R_3$ is hydrogen or ($C_{1-4}$)alkyl and n is 1 or 2, in free base or acid addition salt form, wherein the compound is selected from the group consisting of:

isoquinoline-3-carboxylic acid{(S)-1-azabicyclo[2.2.2]oct-3-yl}-amide,
isoquinoline-3-carboxylic acid{(R)-1-azabicyclo[2.2.2]oct-3-yl}-amide,
6-fluoro-isoquinoline-3-carboxylic acid{(R)azabicyclo[2.2.2]oct-3-yl}-amide,
8-fluoro-isoquinoline-3-carboxylic acid{(R)-1-azabicyclo[2.2.2]oct-3-yl}amide, and
8-fluoro-isoquinoline-3-carboxylic acid{(S)-1-azabicyclo[2.2.2]oct-3-yl}-amide.

2. A process for the preparation of a compound of formula I

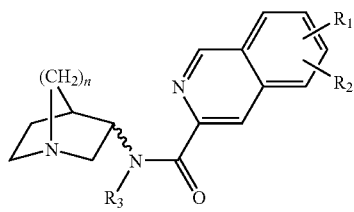

wherein $R_1$ and $R_2$, independently, are hydrogen, ($C_{1-4}$) alkyl, halogen, hydroxy, ($C_{1-4}$)alkoxy, di($C_{1-4}$)alkylamino, ($C_{1-4}$)alkylthio, cyano or trifluoromethyl, $R_3$ is hydrogen or ($C_{1-4}$)alkyl and n is 1 or 2, or a salt thereof, which comprises the step of reacting a compound of formula II

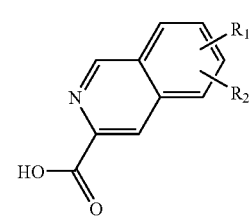

wherein $R_1$ and $R_2$ are as defined above, with a compound of formula III

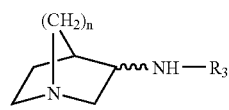

wherein $R_3$ and n are as defined above, and recovering the resulting compound of formula I in free base or acid addition salt form.

3. A pharmaceutical composition comprising a compound of claim 1 in free base or pharmaceutically acceptable acid addition salt form, in association with a pharmaceutical carrier or diluent.

4. A compound of claim 1, wherein the compound is selected from the group consisting of:
isoquinoline-3-carboxylic acid{(S)-1-azabicyclo[2.2.2]oct-3-yl}-amide,
isoquinoline-3-carboxylic acid{(R)-1-azabicyclo[2.2.2]oct-3-yl}-amide,
6-fluoro-isoquinoline-3-carboxylic acid{(R)azabicyclo[2.2.2]oct-3-yl}-amide, and
8-fluoro-isoquinoline-3-carboxylic acid{(R)-1-azabicyclo[2.2.2]oct-3-yl}amide.

5. A compound of claim 1, wherein the compound is isoquinoline-3-carboxylic acid{(S)-1-azabicyclo[2.2.2]oct-3-yl}-amide.

6. A compound of claim 1, wherein the compound is isoquinoline-3-carboxylic acid{(R)-1-azabicyclo[2.2.2]oct-3-yl}-amide.

7. A compound of claim 1, wherein the compound is 6-fluoro-isoquinoline-3-carboxylic acid{(R)-1-azabicyclo[2.2.2]oct-3-yl}amide.

8. A compound of claim 1, wherein the compound is 8-fluoro-isoquinoline-3-carboxylic acid{(R)-1-azabicyclo[2.2.2]oct-3-yl}amide.

9. A compound of claim 1, wherein the compound is 8-fluoro-isoquinoline-3-carboxylic acid{(S)-1-azabicyclo[2.2.2]oct-3-yl}-amide.

10. A compound of formula I

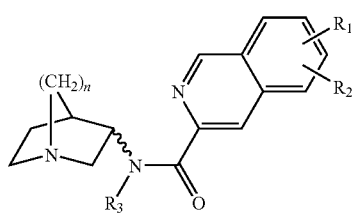

wherein
$R_1$ and $R_2$, independently, are hydrogen or fluorine;
$R_3$ is hydrogen or $(C_{1-4})$alkyl; and
n is 2;
in free base or acid addition salt form.

11. A process for the preparation of a compound of formula I as defined in claim 10, or a salt thereof, which comprises the step of reacting a compound of formula II

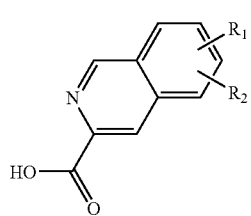

wherein $R_1$ and $R_2$ are as defined in claim 10, with a compound of formula III

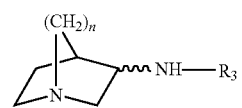

wherein $R_3$ and n are as defined in claim 10, and recovering the resulting compound of formula I in free base or acid addition salt form.

12. A pharmaceutical composition comprising a compound of claim 10 in free base or pharmaceutically acceptable acid addition salt form, in association with a pharmaceutical carrier or diluent.

* * * * *